United States Patent [19]

Hiesinger et al.

[11] 4,367,150
[45] * Jan. 4, 1983

[54] FILTERING METHOD AND APPARATUS

[75] Inventors: Edwin Hiesinger, Jenbach; Klaus Keplinger; Hermann Nessler, both of Innsbruck, all of Austria

[73] Assignee: Inkomag, Basel, Switzerland

[*] Notice: The portion of the term of this patent subsequent to Aug. 25, 1998, has been disclaimed.

[21] Appl. No.: 249,708

[22] Filed: Apr. 1, 1981

Related U.S. Application Data

[62] Division of Ser. No. 62,747, Aug. 1, 1979, Pat. No. 4,285,821, which is a division of Ser. No. 907,628, May 19, 1978, abandoned.

[30] Foreign Application Priority Data

May 20, 1977 [AT] Austria .................................. 3609/77

[51] Int. Cl.³ .............................................. B01D 37/02
[52] U.S. Cl. .................................... 210/777; 210/193; 210/350
[58] Field of Search ............... 210/777, 798, 193, 350, 210/351, 393, 399, 411, 413, 435

[56] References Cited

U.S. PATENT DOCUMENTS

| | | | |
|---|---|---|---|
| 2,403,021 | 7/1946 | Peterson et al. | 210/777 |
| 3,735,872 | 5/1973 | Anderson | 210/193 |
| 3,779,386 | 12/1973 | Ryan | 210/193 |
| 4,285,821 | 8/1981 | Hiesinger et al. | 210/777 |
| 4,297,211 | 10/1981 | Hiesinger et al. | 210/193 |

Primary Examiner—Ivars C. Cintins
Attorney, Agent, or Firm—Karl F. Ross

[57] ABSTRACT

A method of and an apparatus for the filtering of a fluid in which a filter-aid agent of a particulate or fibrous character is floated onto and deposited upon a support fabric in a fluid. The medium to be filtered is then passed through the filter layer formed by this filter aid. The fabric divides the filter chamber into two compartments both of which are flushed with washing liquid which is discharged from the upstream compartment after back-washing through the fabric. During the filtration, a loss of the purified filtrate and a mixture with nonfiltered medium is precluded in that both compartments, after the filtering and cleaning phases, are completely discharged of fluid. The back-washing of the fabric is effected with another fluid.

14 Claims, 22 Drawing Figures

FILTERING METHOD AND APPARATUS

This is a division of application Ser. No. 062,747, filed Aug. 1, 1979, now U.S. Pat. No. 4,285,821, which in turn was a divisional application of Ser. No. 907,628, filed May 19, 1978, now abandoned.

FIELD OF THE INVENTION

The present invention relates to a method of and to an apparatus for the filtering of particles from a fluid, especially the removal of solids from a liquid, and, more particularly, to improvements in the filtering of contaminated water, biological substances and the like.

BACKGROUND OF THE INVENTION

It has already been proposed to provide a process for the removal of particles from a flowing medium in a filter device operating by a repetition of three main working phases. The filter chamber is provided with closable inlet and outlet openings and can be formed with a support fabric for a filter layer, this fabric subdividing the chamber into two compartments. In each deposition phase, a filter-aid agent, i.e. a fibrous or particulate material, is entrained by a carrier medium through the filter cloth from an upstream compartment to a downstream compartment to deposit a layer of this filter aid in the form of a filter layer upon the support fabric. In each filtering phase of the sequence, the medium to be filtered is introduced into the upstream compartment and traverses the filter layer upon which its particles deposit. The purified filtrate is removed from the downstream compartment. The third or final main phase in the operation of such a system is a cleaning phase in which the contaminated filter layer is backwashed from the support fabric and removed from the upstream compartment.

A process of this type has been described in German Pat. No. DT-PS 965 850. In this process, surface water is filtered to remove impurities. In this case, the backwashing uses a clarified or purified liquid, namely, the filtrate from a previous filtering stage.

This filtrate loss during the backwashing to release the deposited filter layer can be considered acceptable only if the filtered medium is not especially valuable or is not available only in limited quantities. This may be the case for water but is usually not the case for other liquids and hence this process has been found to be practical only for water filtration.

A similar process is described in German Pat. No. AT-PS 316 583. In this process, backwashing is carried out with the filtrate in such manner that a mixing of the medium to be filtered with the filtrate during the cleaning phase is unavoidable. Since this process also deals only with the cleaning of water, the disadvantage is only of limited significance.

However, with the filtration of valuable liquids, which are only produced in small quantities, i.e. in a variety of processes in which losses of the filtrate are undesirable and a mixing of the washing medium and the medium to be filtered can occur, problems have been encountered with the prior-art systems.

This is especially the case in the production of wine and beer where filtration is necessary. In such cases, the filter elements must be removed, cleaned, and re-introduced into the processing line if contamination of the filtered product as a result of the backwashing is not to occur.

Such procedures are time-consuming and limit the size of the apparatus which can be utilized because of the need to manipulate the filter surfaces at frequent intervals. It is frequently necessary to provide a large number of filter surfaces to minimize the down time of the apparatus and increase the interval between two cleaning operations.

In filter systems for such comestible materials of relatively high value, the filter-aid agent is usually a high-quality expensive substance, such as kieselguhr (a silica) which is added to the medium during the filter process so that the filter process also involves a progressive increase in the size of the filter layer.

Both this type of filtering operation and the subsequent cleaning have been found to require extremely high operating pressures and the use of such high pressures necessitates the formation of a pressure-resisting filter device. Such filter units, capable of resisting the significantly elevated pressures required by the processes, are extremely expensive, create cleaning difficulties, and can only be operated at high energy cost.

Filter devices are also known for the recovery of solid particles. The residues of the medium to be filtered are removed as far as possible by pressing the filter cake formed on the filter layer. Such a system is described, for example, in Swiss Pat. No. CH-PS 399 422. The filter cake is then washed and dried, e.g. as described in German open application No. DT-OS 1 805 478.

For the pressing of the filter cake, movable walls, e.g. membranes, can be used and can be urged against one another by pressurization of compartments defined between these membranes and other walls of the filter chamber. The filtrate is usually intended to run off through grooves in the movable walls.

After the filter cake has been pressed, the filter device is usually opened and the filter cake removed. Obviously, in such case, it is of no significance that backwashing does not use the filtered medium.

The process there described is not satisfactory when the material removed on the filter layer is contaminated or is not readily handled. It will not be effective, moreover, when a coherent filter cake is not formed.

It is obvious from the foregoing that conventional filter systems, whether they use the backwashing technique or the filter cake removal technique, have disadvantages especially when the processes are intended for the removal of biological materials from a liquid.

OBJECTS OF THE INVENTION

It is, therefore, the prinicpal object of the present invention to provide a method of and an apparatus for the filtering of materials from a liquid whereby the disadvantages of the aforedescribed earlier systems are obviated.

Another object of the invention is to provide a method of and an apparatus for the filtering of substances from a liquid in which the loss of filtrate is minimized and mixing of the various media, especially mixing of the washing medium with the medium to be filtered, is minimized or excluded.

Still another object of the invention is to provide a method of and an apparatus for the improved filtering of water, comestible liquids and the like which minimizes the handling of the deposited materials and which is relatively simple and economical to operate.

Yet another object of the invention is to provide a low-cost apparatus for the improved filtering of solids from liquids which can be fabricated at low capital cost and can be operated, as a filter, with minimal operating cost.

SUMMARY OF THE INVENTION

These objects and others which will become apparent hereinafter are attained, in accordance with the present invention, in a system wherein at least after each filtration and each cleaning phase, the residual fluid media in both compartments of the filter chamber are removed and wherein during each cleaning phase, the cleaning liquid is a substance different from the filtrate and at least in part is bachwashed through the filter cloth and hence dislodges and entrains the filter layer together with the contaminants or solids deposited thereon.

According to the invention, the filter chamber is subdivided into an upstream compartment into which the medium to be filtered is fed, and a downstream compartment from which the filtrate is led away, by a liquid-permeable support cloth upon which the filter layer is adapted to form, in the upstream compartment, during the deposition phase.

The complete emptying of filtrate as well as rinsing medium from both of these compartments, after each working phase involving one of these media, eliminates any possibility of mixing of residues of one of these media with the next to be supplied.

Since the compartments are completely emptied, they are not washed free from the deposited filter-aid (filter layer) and accumulated contaminants by the filtrate, but rather with a rinsing or washing medium which is a substance different from that of the filtrate. For this purpose, it has been found to be advantageous to provide, within the filter chamber, a perforated support or partition upon which the fabric can lie and through which the backwashing fluid is forced from the downstream compartment mentioned earlier.

In a preferred embodiment of the present invention, after each deposition phase, i.e. each phase in which the filter layer is formed by deposition of the filter aid from the carrier medium, residual fluid is removed. In this case, of course, the residual fluid is a residue of the carrier medium.

The process of the present present invention can be carried out with two, preferably three, separate flow schemes:

(a) The deposition phase can be of two types. Thus the medium to be filtered and the carrier medium can be the same substance, i.e. the carrier medium can be filtrate from which the particles of the substance to be filtered have been removed. In this case, the filter aid can be added in a given quantity to previously filtered or otherwise derived medium which is of the same composition as the filtrate. In this case, the inlet opening for the medium to be filtered and for the washing medium, as well as the outlet opening for the washing medium are closed. The carrier medium is introduced through its inlet opening into the first compartment and is distributed over the support fabric, the clear carrier medium, after traversing the fabric, passing through the outlet opening for the filtrate.

When the carrier medium for the filter aid is not intended to be a clear medium of the same composition, the outlet opening for the filtrate is also closed and instead of this outlet opening, a separate outlet opening is provided and is opened. In this case, the residue of the carrier medium is removed from the filter chamber before commencement of the filtration phase.

(b) The medium to be filtered is introduced through the closable inlet opening in the first, upstream compartment in which the filter layer has been formed by the filter aid. The filtrate flows out of the second, downstream compartment via the outlet opening thereof. The contaminants in the filtered medium are deposited on the filter layer. Since both compartments are completely emptied at the conclusion of the filtration phase, a loss of filtrate is impossible.

(c) The third flow scheme is followed by the washing medium. The latter is introduced through an inlet opening in the filter chamber and passes along the underside of the support fabric. It is removed from an outlet in the first or upstream compartment so that the liquid or other washing fluid downstream of the fabric passes through the latter and thus backwashes the filter layer from the support fabric. The filter layer material and the material trapped thereon are entrained away by the backwashing fluid.

During this stage, the inlet openings for the medium to be filtered and the filter aid, and the outlet opening for the filtrate in the second compartment are all closed.

At the end of the cleaning phase, the residues of the washing medium are removed from both compartments so that a sharp separation of the individual stages results and a mixture of the media during transmission between the two phases is excluded. The filter apparatus according to the invention thus is able to be used for the filtration of highly valuable, low-volume media.

The invention is particularly satisfactory when employed for the filtration of liquids with soluble organic components, such as wine, beer, cider and the like. In this case it is advantageous, after removal of the residues of the medium which was filtered and before beginning of the cleaning phase, to sterilize the filter chamber. This eliminates the multiplication of bacterial cultures and prevents plugging of the fabric with time as may result by such bacterial development.

According to another feature of the present invention, the residual media are displaced from the filter chamber by a displacement medium. This displacement medium can be air or another gas.

According to still another feature of the invention, residues of the liquid are removed from both of the compartments by providing each of the compartments with a respective movable wall which can press against the partition.

The delimiting of the compartments by respective movable walls makes it possible to decrease the volume of each compartment by expanding a pressurizable space behind the movable wall and pressing the movable wall against the partition, thereby reducing the volumes of the two compartments on either side of the support fabric to zero.

A filter device according to the present invention is thus formed by providing the filter chamber with a rigid partition which is spanned by the support fabric on which the filter layer is adapted to be formed. An inlet opening for the washing medium is provided in the compartment at the downstream side of the support fabric and, advantageously, both of the compartments are delimited by movable walls, e.g. formed by membranes, in the manner described above.

When the partition is provided with with throughgoing openings, the movable wall on the side of the support fabric provided with the rigid partition having the throughgoing opening is also provided with a multiplicity of rises which fit into and plug these openings as may be required. These openings are thus sealingly closed and, advantageously, the rises can be used to drive out residual liquid from the openings.

The filter apparatus according to the invention is especially for the filtration of wine, beer or like comestible liquids because it allows an effective cleaning of the support fabric and effective replacement of the filter layer without having to disassemble the filter apparatus. Furthermore, an extremely inexpensive filter aid can be used.

Best results have been found in the case of wine, beer and cider when the filter aid consists of cellulose fiber, cotton fibers or the like. A filter aid such as sawdust or wood chips can also be used effectively. The contaminated filter material can be used as fertilizer since these filter-aid substances are biodegradable and thus one need not fear contamination of the environment by disposing of the filter components carried away by the washing liquid.

According to another feature of the invention, the rigid portion of the partition is formed as a grate while the movable wall juxtaposed with this rigid portion of the partition and on the opposite side thereof from the support fabric, can be a rigid plate provided with the aforementioned rises which are dimensioned and configured to fit fully into the throughgoing openings of the grate. Advantageously, these rises are frustopyramidal in configuration and the openings in the grate converge away from the movable wall provided with this displacement plate. By the pressing of the movable wall against the partition, the openings can be sealed as noted above and a continuous support surface can be provided on the side of the partition against which the support fabric lies.

The support fabric is preferably a polyester monofilament wave which can have a mesh width or size between $10\mu$ and $5100\mu$ and we prefer to use the fabric marketed commercially under the name "POLYMON". For the filtering of wine and beer, it has been found that a mesh size of $25\mu$ in the fabric is desirable. Such a fabric is marketed by Schweizerische Seidengazefabrik AC, Zurich, Switzerland, and has a maximum moisture absorption of 0.6%. It has practically no stretchability and hence is highly desirable for the purposes of the present invention.

Another suitable fabric is that marketed under the name "NYBOLT" by Schweizerische Seidengazefabrik AC, Zurich, Switzerland, this fabric being a polyamide 66-monofilament fabric with a mesh width of $5\mu$ to $4000\mu$. Of these fabrics, the fabric with a mesh size of about $20\mu$ has been found to be most advantageous.

According to still another feature of the invention, two inlet openings are provided for the washing liquid, one such opening being disposed on each side of the fabric. The fluid supplied by the opening on the upstream side of the fabric thus serves to entrain the released filter materials through the outlet opening which is also disposed on this side of the fabric and communicates with the upstream compartment.

BRIEF DESCRIPTION OF THE DRAWING

The above and other objects, features and advantages of the present invention will become more readily apparent from the following description, reference being made to the accompanying drawing in which.

SPECIFIC DESCRIPTION

In order to better appreciate the principles of the present invention, FIGS. 1–5 have been provided to diagram the successive steps in the method of the invention. In each al illustrations, are provided with the usual fluid passages and ports necessary for the several operations.

One side 9, the upstream side with respect to the liquid to be filtered, of the perforated partition 5 is provided with a filtering support, e.g. a filter cloth designed to trap the filter-aid agent as will be described below.

The filter aid which may be used in accordance with the principles of the present invention, may be any particulate (pulverulent, fiber or flake) substance which can be entrained and preferably dispersed in a fluid and supported by the cloth layer 9 to form the filter layer. A suitable filter aid is diatomaceous earth. The only requisite for such a filter aid is that it be predominantly of a particle size which is greater than the mesh size of the support cloth so that the filter aid will be trapped upon the filter cloth to form a filter layer which, in turn, will form interstitial passages for the fluid to be filtered of a mean diameter which is less than the diameter of the particles to be filtered out but greater than the molecular size of the filtrate.

Figure 1:
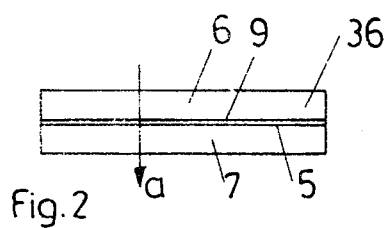
FIGS. 1, 1a, 2, 3, 3a, 4 and 5 are diagrammatic views illustrating the method of the invention in accordance with the principles thereof.

Referring now to FIG. 1, the filter chamber 36 is operated so that a carrier medium, e.g. a carrier liquid, in which a filter aid is dispersed is passed through the filter chamber in the direction of arrow a, i.e. from the upstream compartment 6 through the support cloth 9, the perforated partition 5 and the downstream chamber 7.

The filter-aid particles are thus deposited on the support web 9 to form the filter layer 9a.

Figure 1A:
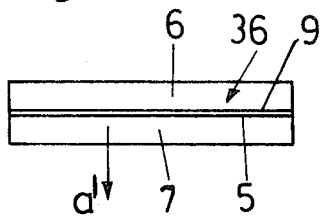
Figure 2:
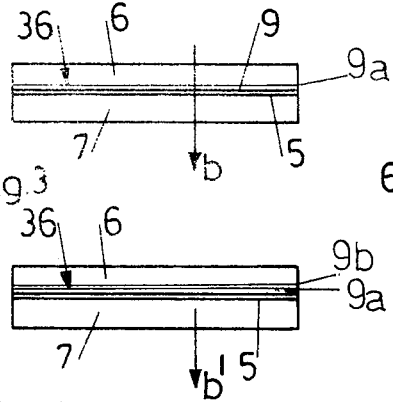

If the carrier medium is previously derived filtrate or can be mixed with the filtrate of the working fluid without a problem, the step illustrated in FIG. 2 follows immediately. However, if the carrier medium and the filtrate of the working fluid are different in nature or cannot be mixed, the step illustrated in FIG. 1a follows that of FIG. 1. This step, shown schematically in FIG. 1a, is a removal of residual carrier fluid as represented by the arrow a' from the filter chamber 36. This removal can be by evacuation from the downstream chamber 7.

Assuming that the carrier medium can be mixed with the filtrate of the working fluid or is of the same composition as the working fluid or through the step illustrated in FIG. 1a has been carried out, the medium to be filtered is then passed through the filter chamber 36 as represented by the arrow b and leaves the latter as cleaned filtrate, the impurities and contaminants having been deposited upon the filter layer 9a as a further layer 9b. The flow of the liquid in FIG. 2 thus also takes place from the upstream chamber 6, through the filter layer 9a, the support fabric 9 and the perforated partition 5, to the downstream chamber 7 from which it is withdrawn.

Figure 3A:
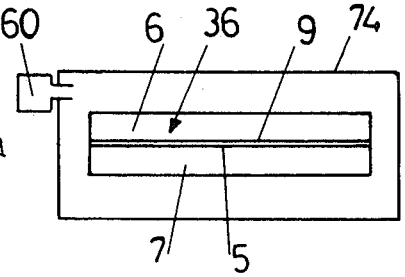
Figure 3:
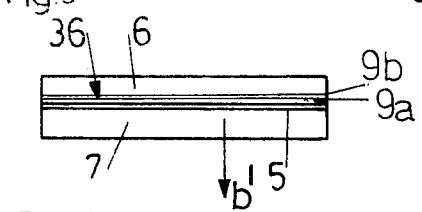

Upon conclusion of the filtration step, i.e. upon the decrease in the rate of flow of filtrate through the filter to a predetermined minimum (indicative of substantial blocking of the passages of the filter) residual filtrate is withdrawn as represented by the arrow b' in FIG. 3.

It is frequently desirable, at this point, and is a preferred mode of realizing the invention, to effect a sterilization of the filter chamber 36. In this case, the filter chamber 36 is placed in a housing 74 and is subjected to sterilization by a microwave transmitter 60 (FIG. 3a).

Figure 4:

Cleaning is then commenced as is shown in FIG. 4 by passing a rinsing or washing medium through the filter chamber as represented by the arrow c. In this step, the washing medium or liquid is passed into the upstream compartment 6 and the downstream compartment 7 from one side of the filter chamber and is removed from the upstream compartment at the opposite side thereof. Thus, a portion of the liquid is passed along the filter side of the partition 6 to entrain the contaminants and the filter aid away while another portion of the liquid backwashes through the partition 5 to assist in dislodging the filter aid and the contaminants (FIG. 4).

Figure 5:
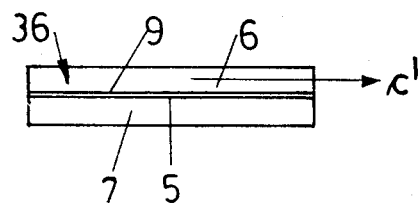

The final step is shown in FIG. 5 and involves the withdrawal at c' of residual washing liquid from the upstream compartment 6.

Figure 6:
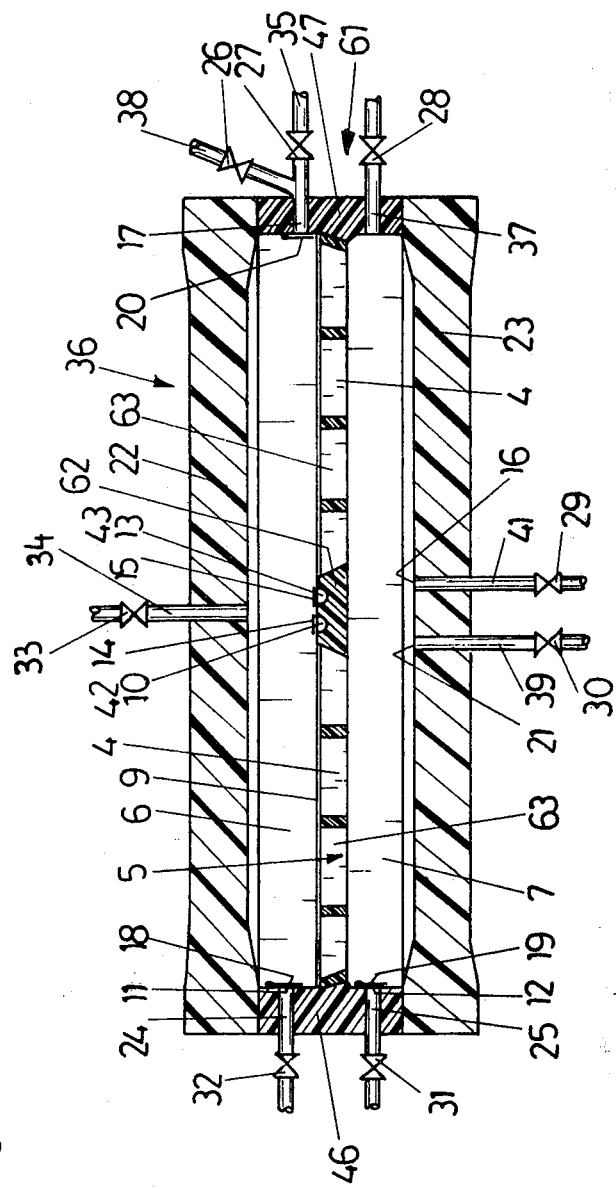
FIG. 6 is a schematic cross-sectional view through a first embodiment of a filter chamber according to the invention.

FIG. 6 shows a filter chamber 36 which can be operated in the steps represented in FIGS. 1-5 in its proper structural form.

The filter chamber 36 of FIG. 6 comprises a bottom plate 23, a frame 61 mounted upon the bottom plate 23 and provided with a central rib 62 and an upper plate 22 resting upon the frame 61. The result is a structure whereby the frame 61 defines with the upper plate 22, the upstream compartment 6 while the frame 61 defines with the lower plate 23, the downstream compartment 7 as previously mentioned.

On both sides of the central rib 62, there are provided replaceable inserts 63 in the form of grates, each of which is covered with a support fabric 9. The central rib 62 and the two inserts 63 form the perforated partition wall 5. The support fabric 9 is thus disposed in the first or upstream compartment 6 and covers the throughgoing openings 4 of the grates 63.

In the central rib 62, there is provided the inlet passage 42 for the medium to be filtered. This passage 42 opens into the upper or first compartment 6 through an inlet bore 10.

After passing through the filter layer which lies upon the support fabric 9, the liquid flows as the clean filtrate into the second compartment 7 and is removed through an outlet bore 16 which communicates with the outlet passage 41 in the bottom plate 23. The inlet opening 10 can be closed by a valve 14 while the outlet passage 16 can be closed by a valve 29.

The washing medium flows through the filter chamber 36 in two parts. One part enters via a valve 31, an inlet passage 25 and an inlet opening 12, the lower compartment 7 and flows through the support fabric 9 to lift the filter layer and the impurities therefrom and carry the filter aid and the impurities out of the system. The outlet is provided by an outlet opening 17 of an outlet passage 35 formed with a valve 27. A sealing lip 20 is formed between the opening 17 and the lateral wall 47 of the frame 61.

The second part of the washing liquid is admitted through the outlet tube 24 via a valve 32 and an inlet opening 11 to the upper compartment 6, a sealing lip 18 being provided between the tube 24 and the wall 26 of the frame 61. A similar sealing lip 19 is provided between the opening 12 of tube 25 and this wall 46.

The liquid stream admitted to the upper chamber 6 serves to carry away the loosened filter aid/contaminant body. This liquid stream also is discharged through the outlet 17. The sealing lips 18 and 19 in the filter chamber 36 ensure that leakage around the tubes will be prevented as long as there is a superatmospheric pressure in the filter chamber 36 during the filter process. The sealing lip 20 has the discharge passage 35 downstream thereof and it is desirable to ensure sealing of this lip by maintaining a counterpressure in the passage 35 by feeding a pressure medium thereto via a valve 26 and a duct 38.

The residual washing liquid from compartment 7 is removed through an outlet opening 21 connected to a duct 39 which can be closed by a valve 30.

The carrier medium which entrains the filter aid onto the fabric 9 is supplied via a feed passage 43 in the central rib 62 and opening into the compartment 6 through a port 13. A valve 15 controls the feed of the carrier medium entraining the filter aid. The carrier medium then passes through the filter cloth, to deposit the filter layer thereon and enters the compartment 7. The filter medium is removed through an outlet opening 16, a duct 41 and the valve 29 provided that it is a liquid other than the working liquid which is to be filtered. When the composition of the carrier medium is the same as the liquid to be filtered, it is discharged through the outlet opening 21.

For complete discharge of the compartments 6 and 7 from residues of the respective media or liquids, an expulsion medium, generally a gas such as air or carbon dioxide, can be admitted via the feed line 34 and its valve 33 and/or via the feed line 37 and its valve 28.

FIGS. 7-17 show a preferred, second embodiment of the present invention.

Figure 7:
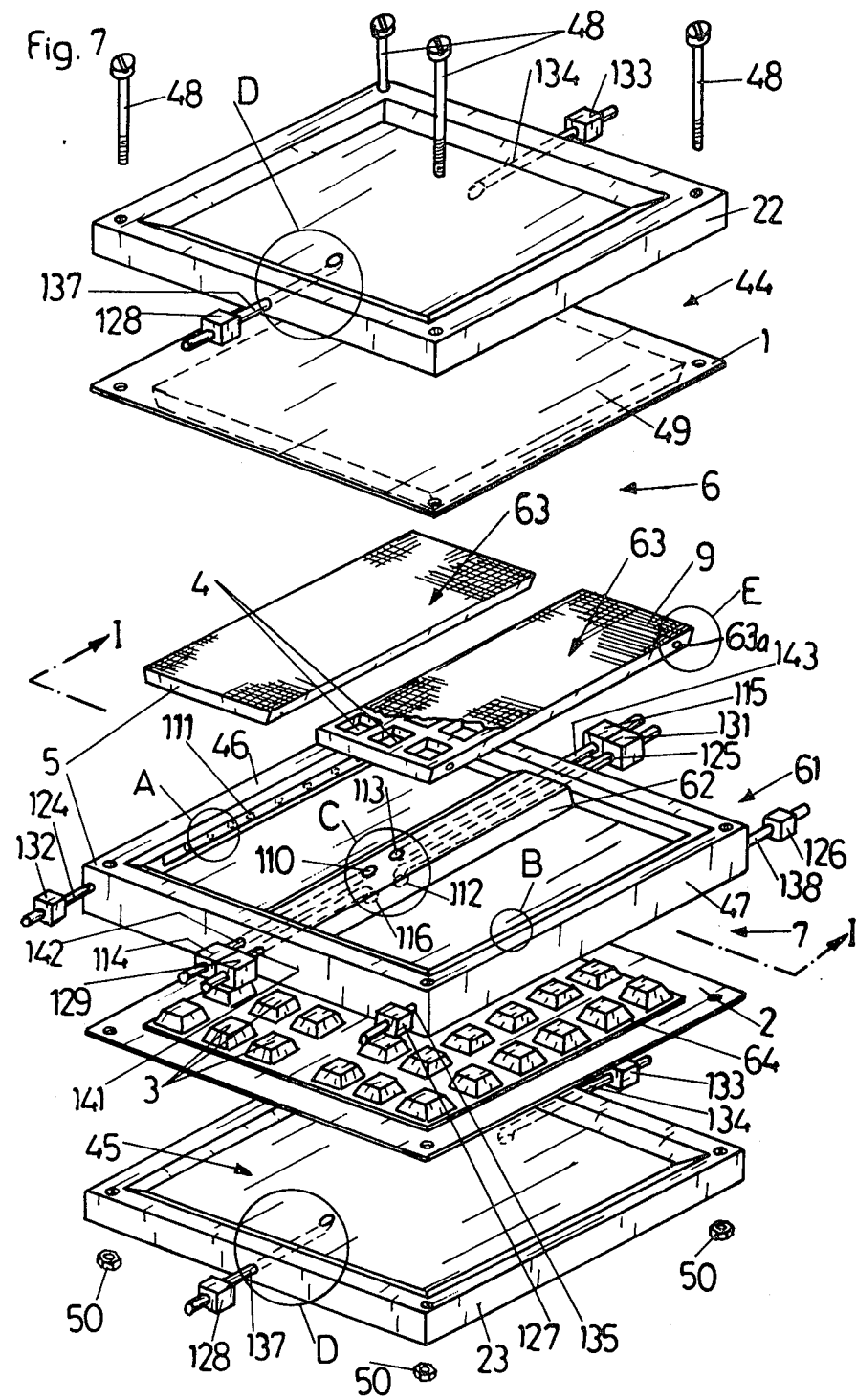
FIG. 7 is an exploded view of a second embodiment thereof, this embodiment constituting the best mode for carrying out the present invention in practice.
Figure 8:
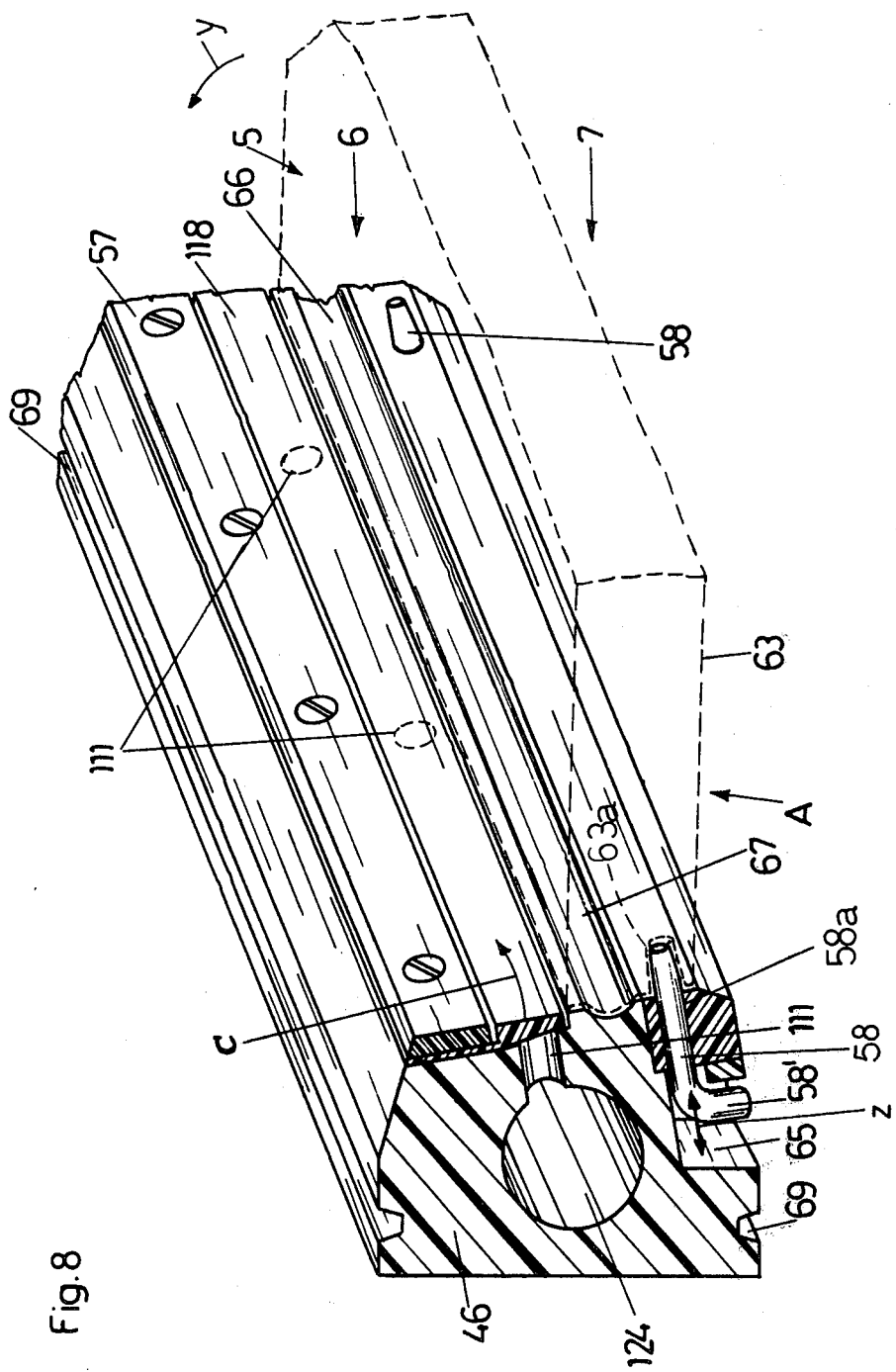
FIGS. 8–12 are detail views, drawn to an enlarged scale, of the portions A–E of FIG. 7.

The structure of the apparatus, from the point of view of its overall configuration, will be apparent from the exploded view of FIG. 7. In FIGS. 7-17, reference numerals identical to those used heretofore have been employed to show identical or equivalent structures in the embodiment under discussion.

Thus, on the tray-shaped base plate 23 there is provided a movable wall, for example, a flexible membrane 2, carrying a displacement plate 64. The latter is formed with a multiplicity of rises or projections 3 which are illustrated to have the configuration of frustopyramides.

The flat edges of the membrane 2 rest upon the upper surfaces of the base plate 23 and are held thereagainst by the horizontal lower faces of the frame 61. Thus the frame 61 rests upon the marginal portions of the membrane 2. The central rib 62 of this frame 61 is formed with four passages whose openings communicate with the interior of the filter chamber 36 via four openings shown at the region C substantially at the center of the rib 62.

The frame 61 receives a pair of grates 63 with respective generally rectangular openings 4, each grate being covered by a tensioned fabric web 9.

The frame 61, the two inserts 63, the fabric 9 and the central rib 62 collectively form the partition 5 which divides the filter chamber 36 into a first upper compartment 6 and a second, lower compartment 7.

The number, distribution and shape of the throughgoing openings 4 in the grate inserts 63 correspond to the number, distribution and shape of the rises 3 on the displacement plate 64.

The assembly also includes an upper movable wall 1 which rests upon the frame 61 and, on its face turned toward the partition, is provided with a displacement plate 49 having a planar surface which is free from rises. An upper cover plate 22 is disposed above the movable wall 1. The entire assembly is held together by means of tie bolts 48 extending through aligned bores at the corners of the assembly parts, and nuts 50 which are threaded onto these bolts.

The bottom plate 23 and the upper plate 22 are of identical configuration so that the filter chambers 36 can be stacked with the upper plate 22 of one filter chamber serving as the bottom plate 22 of the next filter chamber 36 there above.

FIGS. 8–12 illustrate details of the regions A–E. As can be seen from FIG. 8, which is a perspective view of the region A of FIG. 7 in cross section, the left-hand frame member or wall 46 of frame 61 is provided with an inlet passage 124 for the washing medium which is to be passed through the upper compartment 6 in the direction of the arrows in FIG. 4 represented at c. This portion of the washing medium enters through inlet openings 111 which are covered by a resilient strip 118 clamped at 57 by a bar against frame member 46 and deflectable away from this member to admit the washing liquid to compartment 6. Thus, member 118 is equivalent to the sealing lip 18 previously described for the ports 11 of the passages 124. It should be understood that, to the greatest possible extent, where structures are not identical but only equivalent in the several figures, they will be referred to by reference numerals having an additional digit in the hundreds place.

The frame member 46 is, on its side turned toward the filter chamber and below the inlet openings 111, formed with a groove 66 in which a bead 67 of the insert 63 of the partition 5 can engage. Locking of the insert 63 in place is effected by pins 58 which are guided in bores 58a below the groove 66 and have downwardly turned fingers 58' which can be shifted back and forth (arrow c) in a downwardly open recess 65 of member 46. The pins 58 engage in bores 63a shown in broken lines in FIG. 8. To release the replaceable insert 63, it is merely necessary to shift the pins 58 to the left and allow the insert to be swung upwardly (arrow y) and lift it from the frame. Grooves 69 along the upper and lower faces of the frame member 46 can receive sealing beads engageable with the movable walls 1 and 2 or formed directly thereon.

Figure 9:
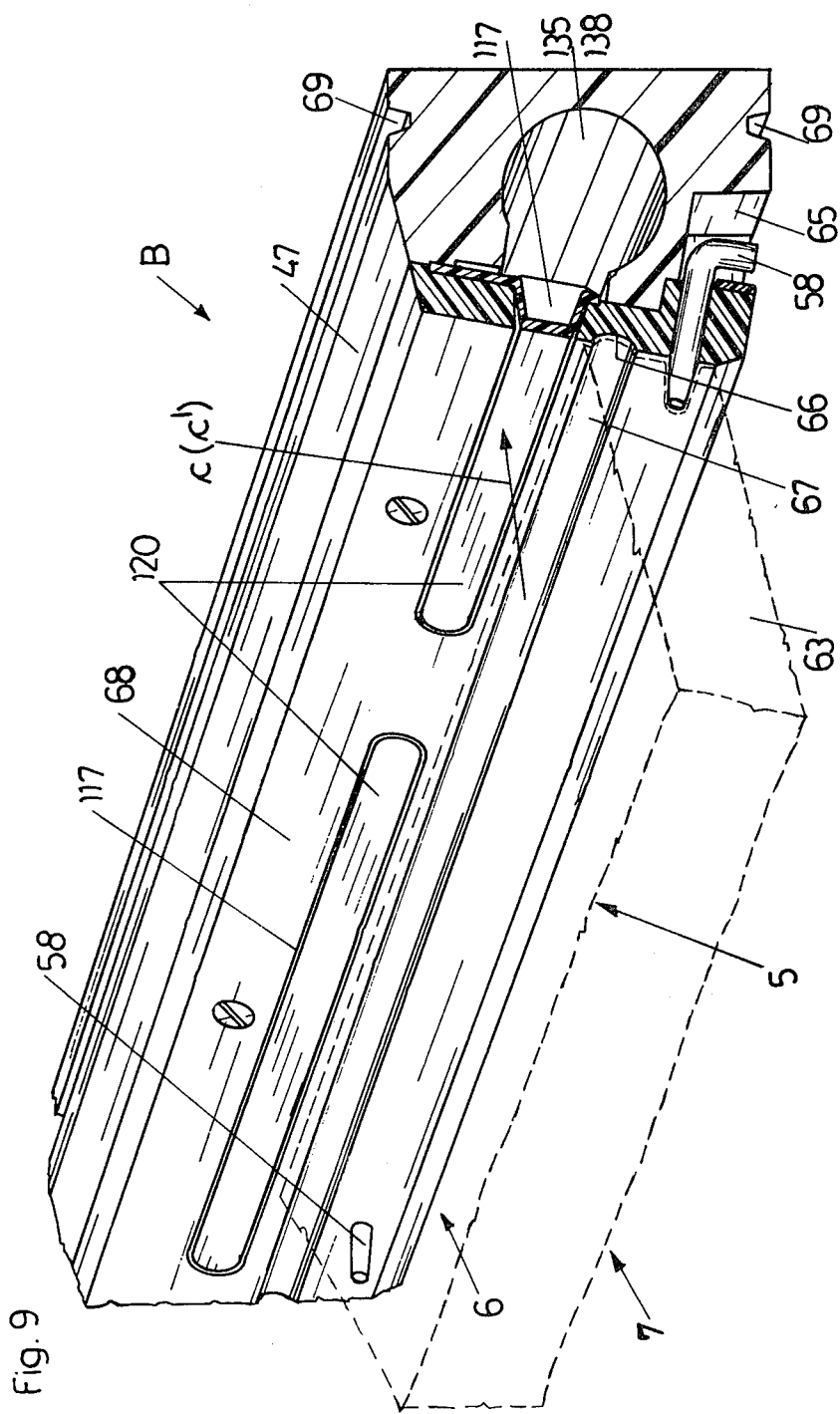

FIG. 9 shows the region B of FIG. 7 in greater detail and hence illustrates the opposite frame member 47. Frame member 47 is provided with the outlet passage 135 (functionally equivalent to passage 35) for the washing medium. The washing medium is discharged from the upper compartment 6 through the outlet openings 117 (here shown as slots but equivalent to the openings 17) in the direction of the arrows c, c' (FIG. 5).

The outlet openings 117 are closable by sealing lips 120 which are held against the frame member 47 by a fastening bar 68 bolted to this frame member 47.

The discharge passage 135 serves alternatively as the supply duct 138 for the pressure medium with the aid of which the sealing lips of the outlet openings 117 are closed during the filtering step and the filter-depositing step, i.e. the stage in which the filter aid is deposited upon the support fabric.

For retaining the insert 63 of the partition 5 against this wall 47, it also is provided with a groove 66 and with pins 58 whose downwardly turned ends can be shifted in a respective recess 65. In this embodiment, the attachment bar 68 extends the full height of the frame member 47 and is provided both with the guide bores for the pins 58 and with the groove 66.

Figure 10:
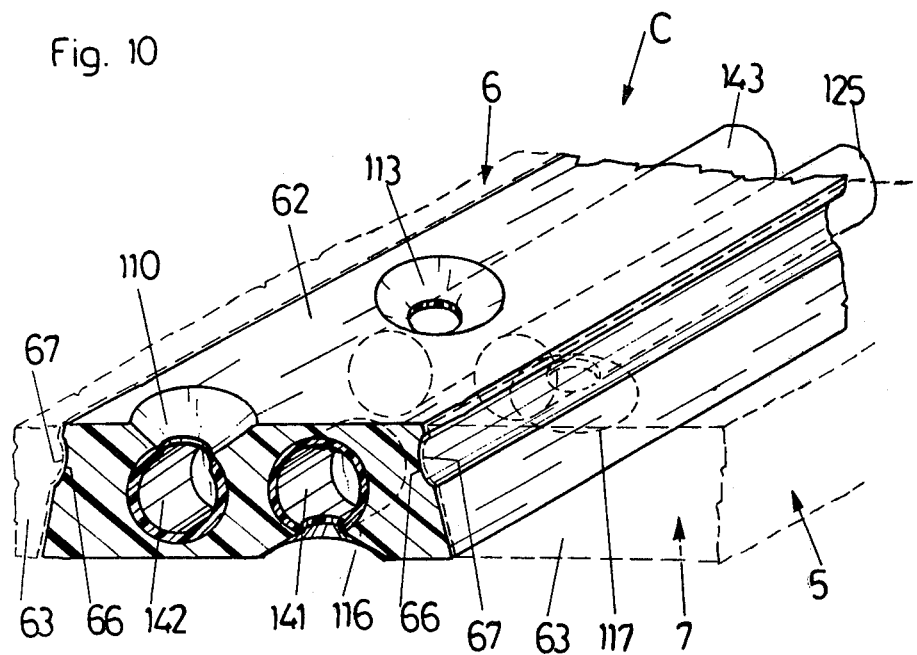

FIG. 10 shows the region C of the central rib 62 (FIG. 7) in detail, as well as a section through this rib. The central rib is formed with a total of four passages which correspond to the passages of FIG. 6 except that they have been identified by reference numerals preceded by a hundreds digit since they differ from the orientation of the corresponding passage.

Thus, an inlet passage 142 for the medium to be filtered opens through an inlet opening 111 into the upper compartment 6. An inlet passage 143 for the carrier medium in which the filter aid is entrained is likewise provided in the rib 62 and terminates in an inlet opening 113. The supply line or passage 125 for the second portion of the rinsing liquid, serving to backwash the fabric support, opens via the outlet port 117 in the lower compartment 7 and an outlet duct or passage 141 for the cleaned filtrate opens via the outlet port 116 in this lower filter compartment 7 also. All four openings are located in the central region C of the rib 62. To enable seating of the insert 63 the opposite lateral flanks of the rib 62 are provided with grooves 66 in which beads 67 of the grates 63 are received. These flanks diverge downwardly to facilitate the swinging of the grates upwardly in the manner previously described.

Figure 11:
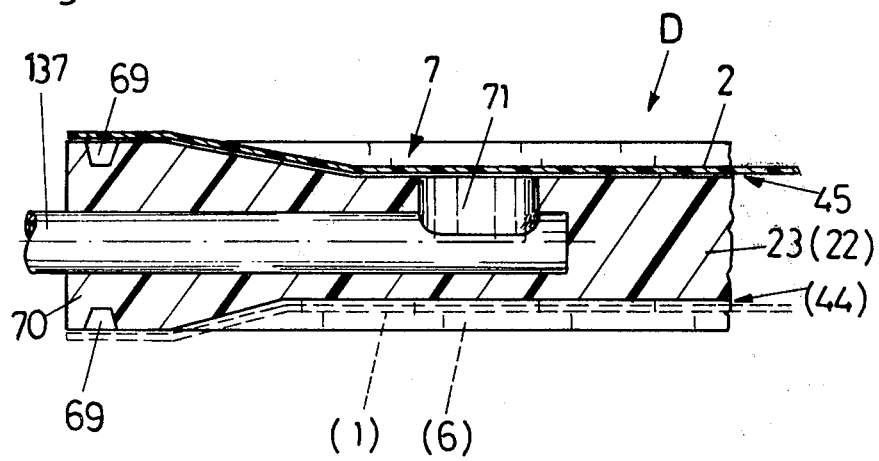

FIG. 11 shows the region D of the bottom plate 23 in cross section, this region corresponding to the upper plate 22 as well since the two plates are identical as has been noted. Each of these plates is formed with a boundary portion or rim 70 which is thick by comparison with the central portion, thereby imparting the tray-shape to the respective plate. The rim 70 is provided with upwardly and downwardly open peripheral grooves 69 which receive seals engageable with the edges of the movable walls or membranes 1 or 2. Between the membrane 1 or 2 and the respective plate 22, 23, there is formed a compartment into which a displacement medium can be admitted through a supply passage 137 and an outlet opening 71. The pressurizable compartment is represented at 44 or 45.

As can be seen better from FIG. 7, each plate 22 or 23 has two such inlet passages 137 opening into the respective compartment 44 or 45 via a corresponding opening 71. Consequently, when fluid is forced under pressure into the respective compartment 44 or 45, the movable wall 1 or 2 is displaced in the direction of the grate and, in the case in which the movable wall 2 carries the plate 64, the rises 3 penetrate into the openings 4 of the grate. The pressurization of the compartment 44, on the other hand, causes the wall 1 to press against the filter layer on the cloth 9.

Figure 12:
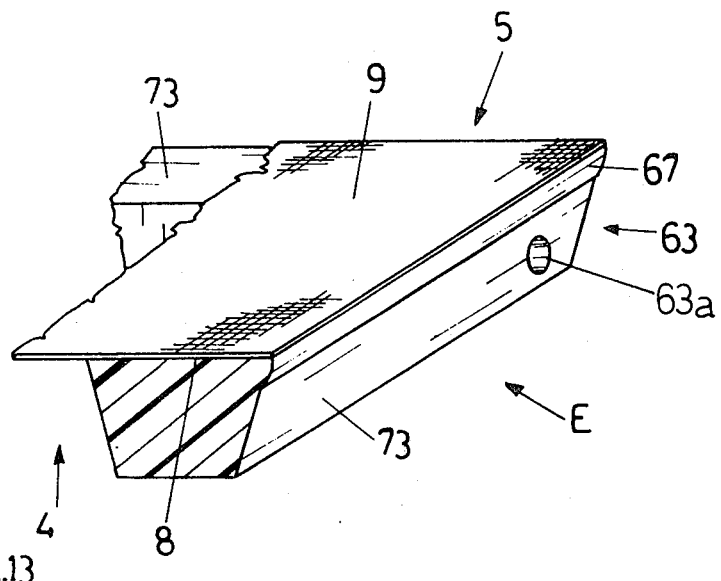

FIG. 12 is a detail view of the region E of one of the insert grates 63 in FIG. 7. FIG. 2 makes it clear that each grate 63 is in the form of a crossbar grate with downwardly converging frustoconical-section bars surrounding each opening 4. The bars 73 along the edges of the grate have been shown in greater detail and can be formed with the bores 63a which receive the pins 58. At least the bars at opposite ends of the grate are provided with beads 67 which can be received in the grooves 66 of the frame member 46, 47 and the central web 62.

The inserts 63 are covered, at least over their upper surfaces, with the support fabric 9 after insertion of the grates 63, these form together with the central rib 62, the partition 5 disposed between the upper compartment 6 and the lower compartment 7 with the support fabric 9 lying in the upper compartment 7.

Each supply and discharge passage is provided with a valve to block it selectively. These valves have only been shown schematically in FIG. 7. However, it should be noted that the valve 126 blocks the supply passage 138 for the pressure medium which acts upon the sealing lip 120. The valve 127 serves to block the discharge passage 135 for the washing medium, the valve 128 blocks the feed passage 137 for the displacement medium in the bottom plate 22, the valve 114 serves to block the feed line 142 for the medium to be filtered, and valve 115 serves to block the feed line 143 for the carrier medium entraining the filter aid.

Naturally, the valves shown in the various figures in the drawing may be located at other places as long as they perform the indicated blocking actions along the respective passages, conduits or ducts. The valves are in part blocking valves and in part checkvalves and valves 126, 128 and 133 are additionally provided with venting facility.

The operation of the filter device shown in FIGS. 1–12 has been illustrated diagrammatically in stages in FIGS. 13–17. In this case, it will be understood that the carrier medium is a filtrate which has already been cleaned by previous passage through the apparatus so that it is not necessary to remove this medium in a separate step (FIG. 1a) before the working liquid is applied.

FIGS. 13–17 may already be considered to be cross sections along line I—I of FIG. 7 although the section is shown to extend through all of the openings in the central rib 62 in spite of the fact that they are not all in line as the correct orientation of these openings in FIG. 10 will demonstrate.

FIRST OPERATING STAGE

Application of Filter Aid

Figure 13:
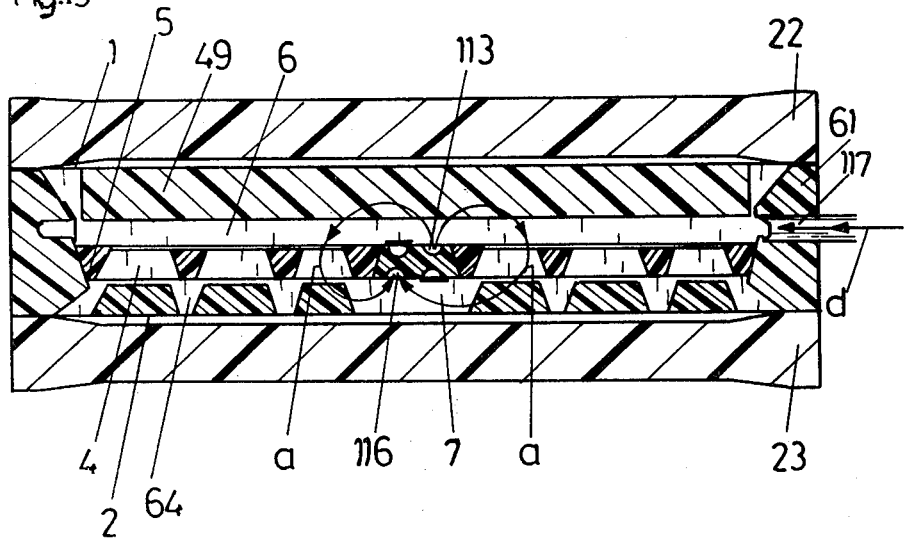
FIGS. 13–17 are schematic cross-sectional views through the apparatus of FIG. 7, taken along the line I—I thereof illustrating the operating modes of this apparatus.
Figure 14:
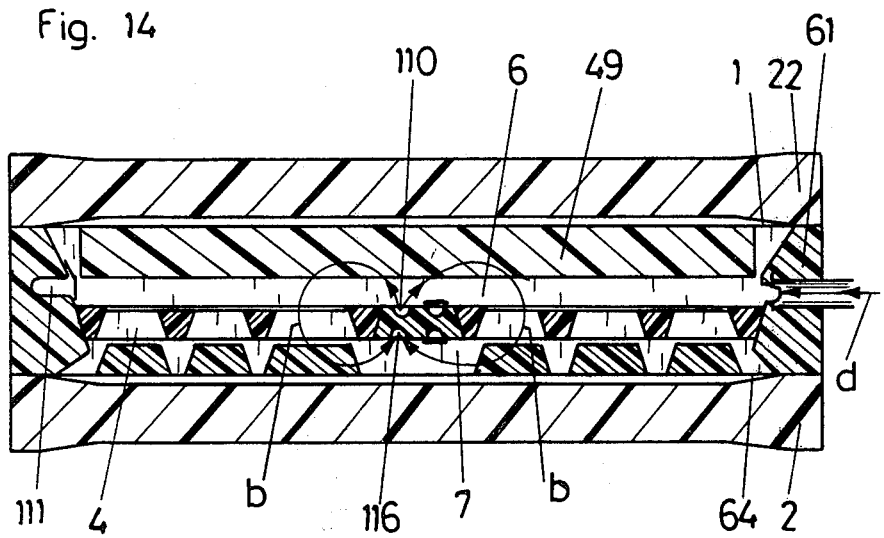

The filter aid material is cellulosic fibers, cotton fibers, sawdust, particles of diatomaceous earth or the like and this first stage is illustrated diagrammatically in FIG. 13.

In this stage, the inlet opening 110 for the medium to be filtered and the openings 111 and 112 for the washing medium are blocked. The sealing lip 118 is under normal pressure and covers the inlet opening 111. Furthermore, the bottom plate 23 and the lower wall 2 define the chamber 45 between them and this chamber is also under normal pressure so that the wall 2 lies upon the bottom plate 23. The opening 117 for the washing liquid is closed by the sealing lip which is pressurized by the elevated pressure in the supply line 138 (arrow d). The pressure chamber 44 defined between the cover plate 22 and the movable wall 1 is under normal pressure.

The carrier liquid in which the filter aid is suspended is introduced via passage 43 of the central ribs 62 and the inlet opening 113 into the upper compartment 6. The filter aid is distributed uniformly over the upper surface of the support fabric 9 to form the filter layer thereon. The medium, from which the filter aid has been removed, flows through the fabric 9 into the lower compartment 7 and is led away, as a clear liquid through the filtrate outlet 116 and the passage 141 also formed in the central rib 62, although along its underside. After the desired thickness of the filter layer has been reached, the supply of the medium is interrupted. The direction of flow is represented by the arrows a.

SECOND OPERATING STAGE

Filtering Contaminated Liquid

The inlet opening 113 is closed and the inlet opening 110 is opened. With the position of wall 1, 2, and sealing lips 118, 120 as described for the first stage, the medium which is contaminated i admitted to the upper compartment 6 via the passage 142 in the central rib 62, and the opening 110. This medium then passes through the filter layer carried by the support layer 9 to deposit its impurities on the filter layer or particles. The pure filtrate passes through the interstices of the filter layer through the support fabric 9, and through the openings 4 of the partition 5 into the lower chamber 7 from which it is discharged via the outlet openings 116 and the passage 141. The accumulation of contaminants upon the filter layer gradually blocks the flow through this layer and hence causes a decrease in the filtering rate and efficiency. The filtering flow is effected in the direction of arrow b in FIG. 14.

THIRD OPERATING STAGE

Figure 15:
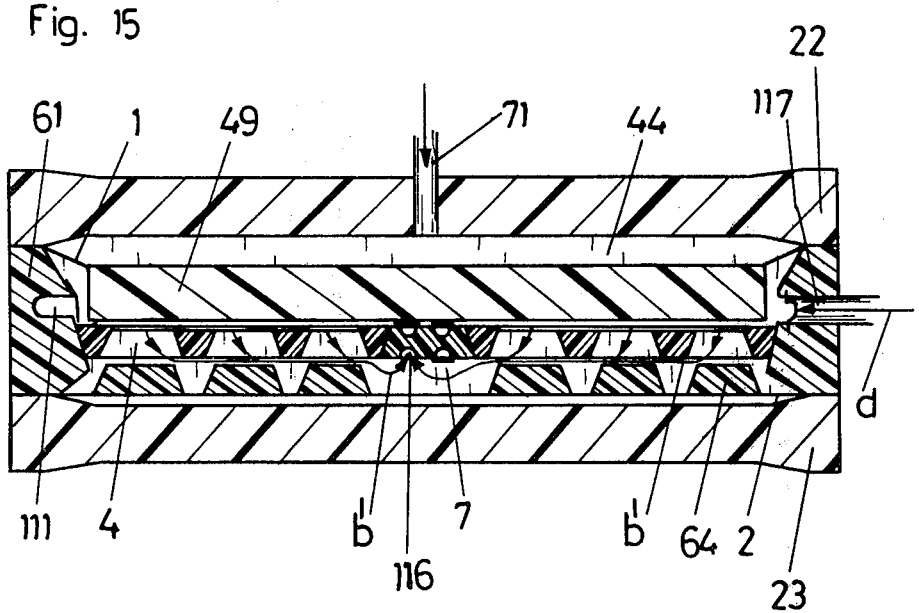
Figure 16:
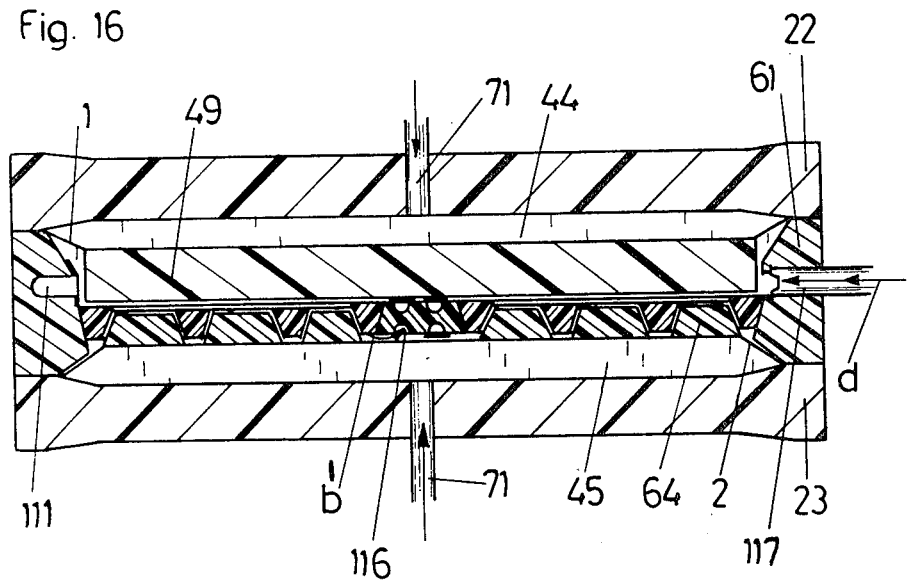

Pressing of the Contaminated Filter Layer (FIGS. 15 and 16)

In this stage the body or layer of contaminants, the layer of filter aid and the sheet of fabric upon which the filter aid is deposited, are collectively pressed. This is especially desirable in the system of the present invention since it can be carried out without the expensive equipment and systems hitherto required in the filtering of wine, beer or other comestibles from a sludge or scum in a vessel. Naturally, pressing may also be desirable where it is economical because of the value of the filtrate or is desirable as a treatment of the contaminating substance. This stage may be used but also can be omitted when the filter system is employed for the clarification of water.

The supply of the liquid to be filtered is interrupted by blocking the opening 110. The other parts and valves remain unchanged except that valve 133 is opened and the chamber 44 is pressurized. The movable wall 1 is applied to the filter layer to press the same against the partition 5. The trapped filtrate flows into the lower chamber 7 and out through the opening 116 in the direction of arrows b' (FIG. 15).

After this pressing stage and again while all of the parts are in the positions originally described, valve 128 is opened and the pressure medium is delivered to the lower pressure chamber 45 to displace the movable wall 1 and the displacement plate 64 upwardly until its rises 3 penetrate into the openings 4 in the partition 5. FIG. 16 shows the position of this lower plate just before complete expansion of the chamber 45. Since, as has been noted, only the outlet 116 is open and a backwashing into the upper chamber 6 is prevented by the wall 1 applied to the top of the filter, all residue of the filtrate passes entirely through the outlet 116 and the passage 141 as represented by the arrows c''. With complete expansion of pressure chamber 45, the movable wall 2 is pressed against the partition 5 and the rises 3 completely fill the openings 4. The feed passages for the pressure medium into the chambers 44 and 45 have been illustrated in detail in FIG. 11 and are only schematically shown in FIGS. 13 to 17.

FOURTH OPERATING STAGE

Sterilization

Especially for the filtration of media containing organic impurities or particles, it is desirable to limit bacterial reproduction by sterilization of the filter chamber. This sterilization can be carried out most effectively after the pressing stage previously described. Reference may be made to the schematic illustration of FIG. 3a in this respect. The outlet opening 116 for the filtrate is first closed and the pressurizable chambers 44 and 45 are drained so that the movable walls 1 and 2 return to their original positions (FIG. 13) and separate themselves from the partition 5. The pressure in supply line 138 is reduced so that the sealing lip 120 no longer blocks the outlet 117. The sterilization is effected with microwaves in a housing 74 surrounding the filter chamber and designed to reflect microwaves. The inlet and outlet conduits are composed of metal so that they are not penetrated by the microwaves. However, the remainder of the filter chamber is composed of synthetic resin which is readily penetrated by the microwaves to ensure complete sterilization. Residual moisture in the contaminants is heated by the microwaves and vaporized, thereby destroying all micro-organisms in the impurities. The media in the inlet and outlet passages, however, are not heated.

FIFTH OPERATING STAGE

Cleaning

The fifth operating stage, cleaning, is preferably carried out in two steps.

Figure 17:
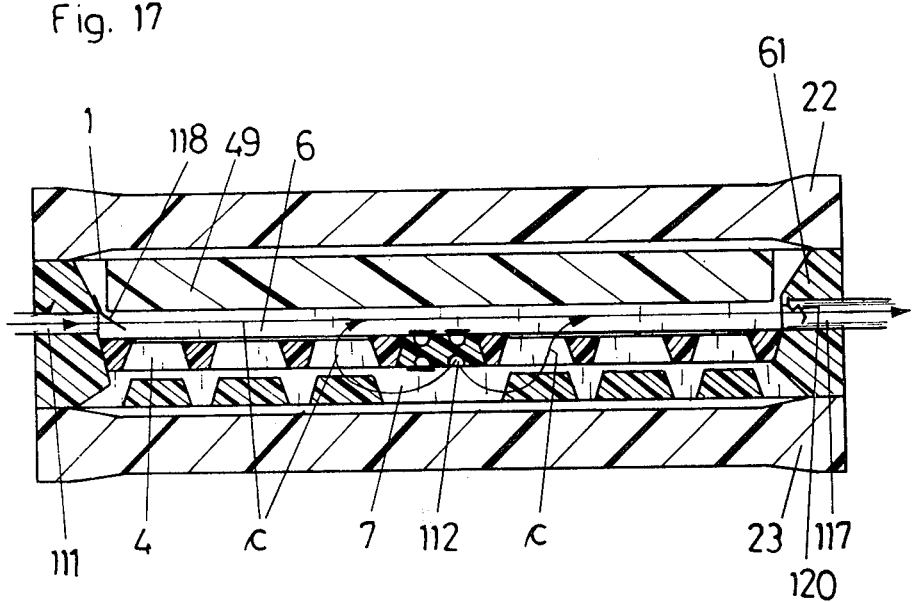

In the first cleaning step, represented diagrammatically in FIG. 17, the support fabric is backwashed with the washing medium. To the extent that it has not been sterilized, the filter chamber is isolated, i.e. by blocking the outlet opening 116. The pressure in the compartments 44 and 45 and in the feed line 138 are reduced to depressurize the movable walls 1 and 2 and the sealing lip 120. The inlet opening 112 for the rinsing or washing medium is opened and the washing liquid flows in via passage 125 to the central rib 62 from which it is supplied to the lower compartment 7. The only free path for the washing medium is thus through the passages in the partition 5 and the mesh of the fabric 9 and thus this liquid is passed into the upper compartment 6 in the course of which it lifts the filter layer from the support fabric.

The washing medium flows through the outlet openings 117 into the outlet passage 135, thereby carrying the contaminated filter layer therewith in the direction of arrow c.

In the second cleaning stage, which ensures total discharge of the contaminated filter material, additional washing medium is introduced through the inlet opening 111 upon the lifting of the sealing lip 118 from the feed conduit 124. The liquid is thus admitted into the upper compartment 6 at one side thereof.

This part of the washing liquid flows along the upper surface of the support fabric 7 to the outlet opening 117 to ensure removal of even the last residues of the filter layer. The washing medium for the first cleaning stage is preferably water while the sparging medium for the second cleaning stage is preferably compressed air which can be shut through the upper compartment 6 in pulses.

To terminate the second cleaning stage, the inlet opening 112 for the rinsing medium which is introduced in the second chamber, is closed and the valve 128 for the lower pressurizable chamber 45 is opened. The movable wall 2 is lifted and the rises 3 penetrate into the openings 4 of the grates 63 to seal these openings. The residual washing liquid in compartment 7 is thus forced completely through the fabric into the upper compartment 6. The inlet opening 111 is closed by the sealing lip 118 to interrupt the supply of the washing liquid by the feed duct 124. The compartment 44 is now pressurized to drive wall 1 downwardly onto the partition 5. The residual liquid is therefore driven out through the still-open outlet 117 whereupon sealing lip 120 closes the outlet 117. The cleaning phase is thereby terminated, and after discharge of pressure from the chambers 44 and 45, the process can be repeated with a deposit of a new layer of the filter 8 upon the fabric.

Figure 18:
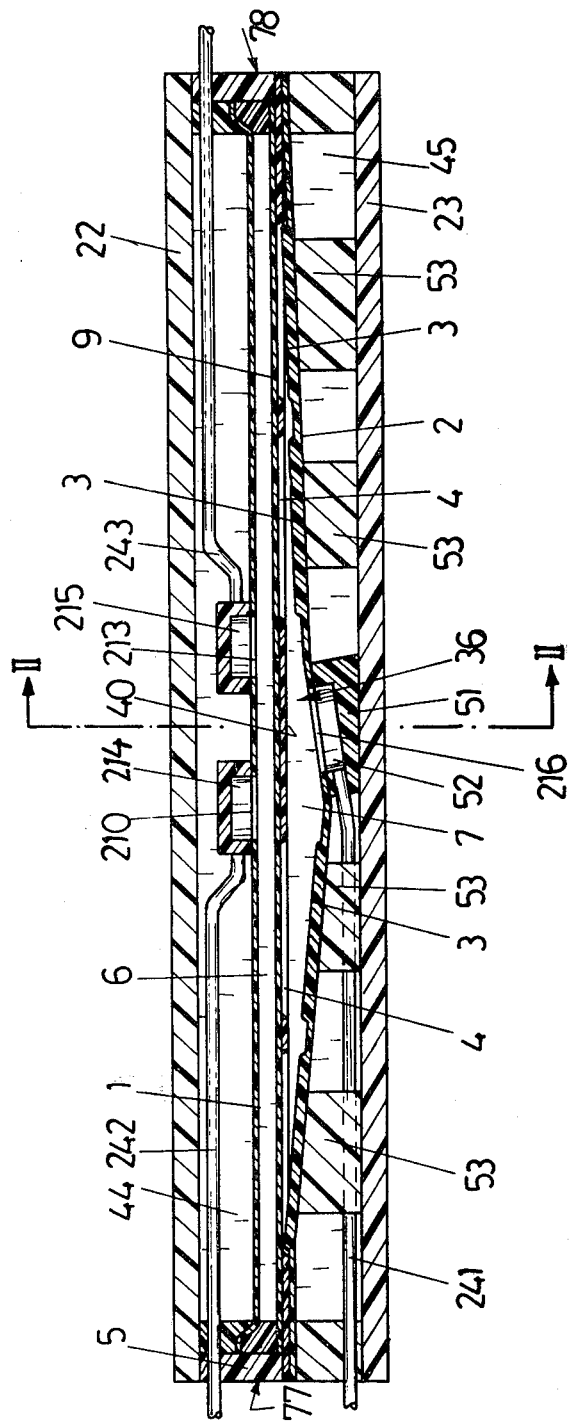
FIG. 18 is a cross-sectional view through a third embodiment of the invention.
Figure 19:
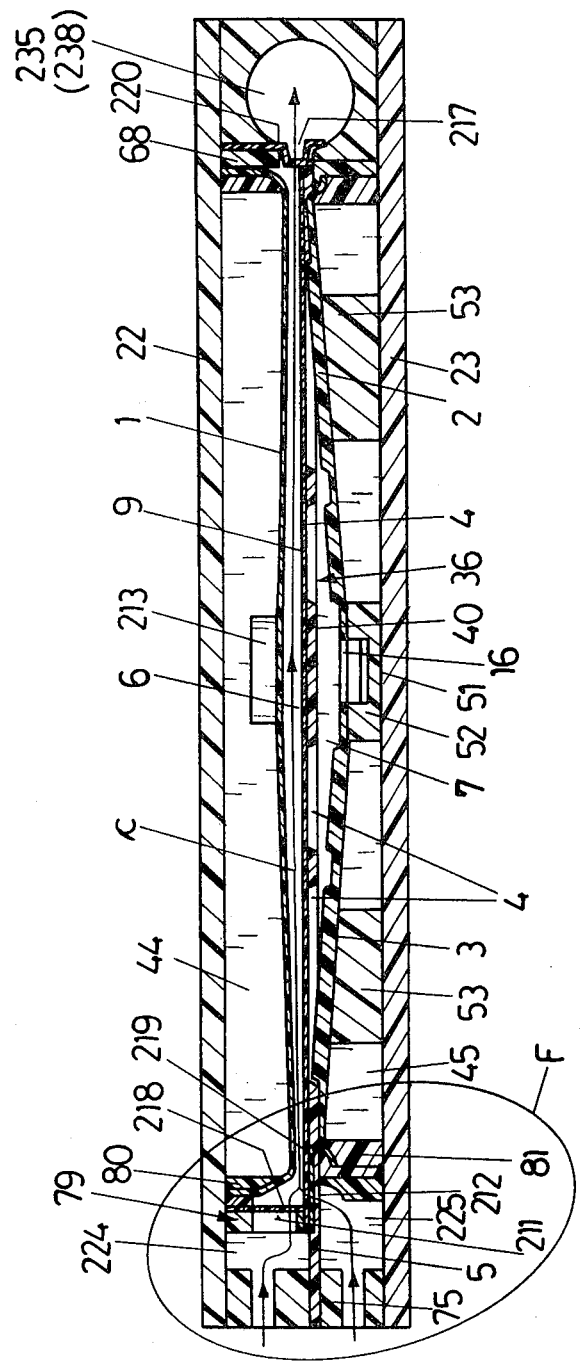
FIG. 19 is a cross-sectional view taken along the line II—II of FIG. 18.
Figure 20:
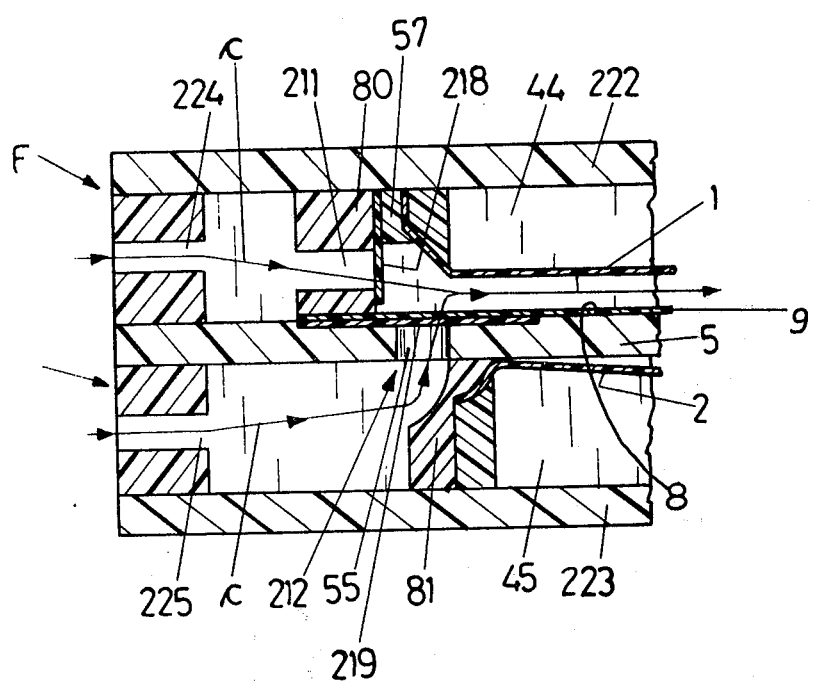
FIG. 20 is a detail view, also drawn to an enlarged scale of the region F of FIG. 19.

FIGS. 18–20 shows a third embodiment of the invention and in these figures structure similar to those of previous figures has been represented by similar reference numerals preceded by a 2 in the hundred digit place.

In this embodiment, the filter chamber is constituted from a bottom plate 223, a cover plate 222 and lateral walls 75–78. Preferably the chamber is assembled from two tray-shaped structures which are disposed with their concavities turned toward one another.

At a reduced distance from the side walls 75, there is disposed a parallel intermediate wall which is subdivided into an upper rib 80 and a lower rib 81, these ribs together with the side wall 75 and portions of the partition 5, the bottom plate 223 and the cover plate 222 from the feed ducts 224 and 225 which supply the washing medium. The discharge of the washing medium is effected through the duct 235 in the lateral wall 76, the duct 235 serving alternatively as a feed duct 238 for the pressure medium which acts upon the sealing lip 220.

Substantially midway between the cover plate 222 and the bottom plate 223, the partition 5 is provided in the configuration described previously, i.e. from grates with throughgoing openings. The ribs 80 and 81 of the partition and the lateral walls 76–78 serve as edge retainers for the movable walls 1 and 2 which are constituted as membranes. The movable walls 1 and 2 flank the filter chamber 36 in which filtration is effected. The partition 5 divides the filter chamber 36 into the two compartments 6 and 7 which are interconnected by the throughgoing openings 4 of the grates and the volumes of the spaces between the walls 1 and 2 and the partition 5 are variable to change the effective volumes of these compartments.

When the partition 5 has relatively large throughgoing openings and broad ribs, it is advantageous to provide ribs which extend in the direction in which the washing medium passes (arrow c). These ribs can be formed in the upper surface 8 of the partition 5. This eliminates any possibility that the support web 9 will sag in an unsupported manner through the openings.

The openings 4 of the partition 5 widen downwardly and preferably are completely filled by the recess 3 upon upward displacement of the flexible wall 2 upon pressurization of the chamber therebelow. This gives rise to a closed surface 8 of the partition upon which the fabric rests and blocks completely any passage of the washing agent into the lower compartment 7.

In the central region of the partition 5, there is provided a zone without openings 4, i.e. with a widened rib 40 of the grate. This widened rib closes the outlet opening 216 for the filtrate which is provided in the wall 2 at a central region thereof. Such closure is effected when the wall 2 is deflected upwardly against this rib 40.

In the absence of pressurization below the wall 2, the latter sags under the weight of the body forming the outlet 216 and the passage 241, downwardly. This body 52 is generally L-shaped and has a beveled or inclined seating surface 51 adapted to reset upon the bottom plate 223 (see FIG. 18). The lower wall 2 thus forms a funnel-like outlet for the filtrate enabling the same to drain into the body 52 and downwardly therefrom to the left as has been illustrated in FIG. 18.

The bottom plate 223 can be formed with a number of support elements 53 upon which the flexible wall 2 can rest to bring about the inclination of this wall toward the center thereof. This eliminates the possibility that filtrate residue will remain between the rises 3.

The upper movable wall 1 is likewise provided in its central region with inlet openings 210, 213 for the passages 242, 243 which are provided with checkvalves 214 and 215.

In this case, the conduit 242 serves as an inlet for the medium to be filtered while the conduit 243 functions as the inlet for the carrier fluid in which the filter-aid material is suspended. The carrier in this embodiment as well can be pure liquid or liquid from which the contaminants have been removed, i.e. filtered filtrate. This medium is discharged through the outlet opening 216 from the filter chamber 36.

The washing medium passes out of the upper inlet 224 (FIG. 19) through the inlet opening 211 and out of the lower passage 225 through the inlet opening 212 into the upper compartment 6 and from the latter, via the outlet opening 217, into the outlet passage 235.

As can be seen from FIG. 20, which shows in detail the region F of FIG. 19, the inlet opening 212 is preferably formed by a row of slits or holes 55 in the partition 5. The inlet opening 211 is formed by a row of slits or holes in the rib 80. To block the inlet openings 211 and 212 and the outlet opening 217, the sealing lips 218, 219 and 220 are provided.

The blocking of the inlet opening 212 (slits 55) in the partition wall 5 is effected by the sealing lip 219 (FIG. 20) which is affixed to the upper surface of the partition 5 whereby the sealing lip 219 is disposed between the partition 5 and the support fabric 9. The washing medium fed through the inlet opening 212 lifts the sealing lip 219 and, to a slight degree, the support fabric 9, and flows between the support fabric 9 and the partition 5 in the first compartment 6. Since the openings 4 have previously been blocked, this liquid flow between the surface 8 and the fabric 9 serves to backwash through the fabric and to dislodge the filter layer with the contaminants thereof.

As has been indicated before, the cleaning steps can be carried out one after another without significant time delay, thereby reducing the downtime of the apparatus even after a long period of use.

We prefer to use as the filter aid materials which in themselves are not detrimental to the environment and which can be biodegradable. Suitable materials for this purpose are cellulose fibers and sawdust or wood chips which, together with the contaminants deposited in the filter layer, can be used as fertilizer. However, it is also possible to recover the filter aid by the washing process.

The system of the present invention has been found to be effective even with fluids having a high solids content since replacement of the filter layer can be effected whenever necessary and in a simple and economic manner. The filter fabric 9 is preferably a woven synthetic-resin fabric, preferably of polyester monofilament with a mesh size of about 25 microns.

The filter device of the present invention has been found to be especially effective in the production of wine, beer and cider, for the purification of water and for removing solids from other suspensions normally considered difficult to filter. It can also be used for the recovery of aerosols from gases. It may be used in chemical technology or laboratory work for the filtration of various liquids, especially since it allows the choice of washing medium, carrier medium, filter aid, etc. The operating pressure in the filter can be less than 2 bars and preferably is about 1.4 bars. The operating pressure for the washing medium can remain less than 5 bars and can be below 4 bars if desired. The pressures developed in the chambers 44 and 45 should be, at a maximum, also in this range. The filter chamber can be fabricated from synthetic resin thereby enabling sterilization by microwaves.

For most purposes it is sufficient to connect the filter chamber to water lines operating at usual mains pressures in which the water can thus serve as the pressure medium for the chambers 44 and 45, as the medium for closing the sealing lips 20, 120, 220, and as the washing medium. Naturally, the pressurizing and/or washing medium can be compressed air or the like.

The simple construction of the filter device of the present invention and the fact that it is practically maintenance free, serves as a basis for its use in a variety of sizes for all of the purposes described, both on a laboratory level and for industrial applications. For water purification, large filter units are preferred whereas for wine and beer production medium size filters can be provided. Household uses will require small size units which can be employed, for example, for the filtration of home-pressed fruit juices.

Naturally other applications can be conceived of without difficulty. For instance, the filter device can be used for extraction of materials with the extract powder serving in whole or in part as a filter aid and being traver Control of the phase sequence can be carried out automatically without difficulty with conventional control and timing devices and a plurality of filters may be assembled together as suggested previously to provide a particularly space-saving stacked structure. Auxiliary devices such as pumps for the medium to be filtered can be made relatively small.

SPECIFIC EXAMPLE

The following table is illustrative of the best mode currently known to us for carrying out the invention in practice. The filter aid was cellulose fibers.

|  | Filter Aid in g/l Carrier Medium | Fabric Type N = Polyamide 20 μm P = Polyester 20 μm | Deposition Time sec | Filtration Time in sec/l clear filtrate | | | | | Pump Pressure bar |
|---|---|---|---|---|---|---|---|---|---|
|  |  |  |  | 0-2 | 2-4 | 4-6 | 6-8 | 8-10 |  |
|  |  |  |  |  | Filtration Time min | | | |  |
| Crude Wine | ½ | P | 30 | 15 | 16 | 16 | 19 | 27 | 1.6 |
|  | 1 | N | 30 | 12 | 16 | 22 | 30 | 37 | 1.6 |
| Beer without | ½ | N | 30 | 15.5 | 27 | 36 | 47 | 61 | 1.6 |
| Counterpressure (Crude Beer) | 1 | N | 30 | 24 | 26 | 36 | 49 | 61 | 1.6 |
|  | 2 | N | 120 | 27 | 33 | 37 | 44 | 52 | 1.6 |
| Beer With Counterpressure 2.0 bar (Crude Beer) | 1 | N | 35 | 40 | 51 | 67 | 90 | 120 | 2.5 |
|  | 2 | P | 35 | 60 | — | 90 | — | 120 | 2.5 |
| Stream Water Very Contaminated | 1 | N | 30 | 14 | 14.5 | 15 | 15.5 | 16 | 1.6 |
| Crude Wine-Vinegar | 1 | N | 30 | 11 | 11.5 | 11.5 | 12 | 12 | 1.6 |

The cleaning duration was on the average 30 seconds.
The filter surface was 0.1 m²

We claim:
1. A method of filtering which comprises:
(a) partitioning a filter chamber with a fluid-permeable planar support fabric into a single upstream compartment and a single downstream compartment, said planar support fabric forming a horizontal partition;
(b) entraining onto said support fabric in said upstream compartment a particulate filter-aid layer by suspending particles of a filter-aid material in a carrier medium, introducing said carrier medium into said upstream compartment, and passing said carrier medium through said fabric whereby said particles form said layer;
(c) discharging the carrier medium of step (b) from said chamber downstream of said support fabric, and removing any residues of the carrier medium completely from said chamber by pressing said support fabric between a pair of movable walls thereby minimizing the volumes of said compartments so that removal of carrier medium from said upstream compartment is completed prior to complete removal of carrier medium from said downstream compartment;
(d) introducing a filterable medium into said upstream compartment, and passing said filterable medium through said layer and said support fabric from said upstream compartment to said downstream compartment, thereby depositing impurities contained in said filterable medium on said layer and enabling pure filtrate to enter said downstream compartment;
(e) discharging the filterable medium of step (d) from said upstream compartment and discharging the pure filtrate downstream from said downstream compartment, and then drawing any residues of said filterable medium completely from said chamber so that removal of such residues from said upstream compartment is completed prior to complete removal of the residues from the downstream compartment;
(f) thereafter introducing a washing medium into said chamber and to the downstream side of said fabric and thereby backwashing said layer from said fabric and entraining material of said layer backwashed from said fabric out of said upstream compartment with the washing medium;
(g) discharging the washing medium used in step (f) from said chamber and removing any residues of said washing medium completely from said chamber; and
(h) thereafter repeating steps (b) through (g).

2. A method of filtering which comprises:
(a) partitioning a filter chamber with a fluid-permeable planar support fabric into a single upstream compartment and a single downstream compartment, said planar support fabric forming a horizontal partition;
(b) entraining onto said support fabric in said upstream compartment a particulate filter-aid layer by suspending particles of a filter-aid material in a carrier medium, introducing said carrier medium into said upstream compartment, and passing said carrier medium through said fabric whereby said particles form said layer;
(c) discharging the carrier medium of step (b) from said chamber downstream of said support fabric, and removing any residues of the carrier medium completely from said chamber so that removal of carrier medium from said upstream compartment is completed prior to complete removal of carrier medium from said downstream compartment;
(d) introducing a filterable medium into said upstream compartment, and passing said filterable medium through said layer and said support fabric from said upstream compartment to said downstream compartment, thereby depositing impurities contained in said filterable medium on said layer and enabling pure filtrate to enter said downstream compartment;
(e) discharging the filterable medium of step (d) from said upstream compartment and discharging the pure filtrate downstream from said downstream compartment, and then drawing any residues of said filterable medium completely from said chamber by a displacement fluid so that removal of such residues from said upstream compartment is completed prior to complete removal of the residues from the downstream compartment;
(f) thereafter introducing a washing medium into said chamber and to the downstream side of said fabric and thereby backwashing said layer from said fabric and entraining material of said layer backwashed from said fabric out of said upstream compartment with the washing medium;

(g) discharging the washing medium used in step (f) from said chamber and removing any residues of said washing medium completely from said chamber; and (h) thereafter repeating steps (b) through (g).

3. A method of filtering which comprises:

(a) partitioning a filter chamber with a fluid-permeable planar support fabric into a single upstream compartment and a single downstream compartment, said planar support fabric forming a horizontal partition;

(b) entraining onto said support fabric in said upstream compartment a particulate filter-aid layer by suspending particles of a filter-aid material in a carrier medium, introducing said carrier medium into said upstream compartment, and passing said carrier medium through said fabric whereby said particles form said layer;

(c) discharging the carrier medium of step (b) from said chamber downstream of said support fabric, and removing any residues of the carrier medium completely from said chamber so that removal of carrier medium from said upstream compartment is completed prior to complete removal of carrier medium from said downstream compartment;

(d) introducing a filterable medium into said upstream compartment, and passing said filterable medium through said layer and said support fabric from said upstream compartment to said downstream compartment, thereby depositing impurities contained in said filterable medium on said layer and enabling pure filtrate to enter said downstream compartment;

(e) discharging the filterable medium of step (d) from said upstream compartment and discharging the pure filtrate downstream from said downstream compartment, and then drawing any residues of said filterable medium completely from said chamber so that removal of such residues from said upstream compartment is completed prior to complete removal of the residues from the downstream compartment;

(f) thereafter introducing a washing medium into said chamber and to the downstream side of said fabric and thereby backwashing said layer from said fabric and entraining material of said layer backwashed from said fabric out of said upstream compartment with the washing medium;

(g) discharging the washing medium used in step (f) from said chamber and removing any residues of said washing medium completely from said chamber by a displacement fluid; and (h) thereafter repeating steps (b) through (g).

4. The method defined in claim 1, 2 or claim 3 wherein the carrier medium of step (b) is different from the filterable medium.

5. The method defined in claim 1, 2 or 3 wherein subsequent to step (d) and prior to step (e), said filter chamber is sterilized.

6. A filtering apparatus comprising:
a housing defining a horizontal filtering chamber;
a rigid horizontal partition extending through said chamber and subdividing same into an upstream compartment and a downstream compartment communicating with said upstream compartment via throughgoing openings formed in said partition;

a support fabric overlying said partition and permeable to a fluid, said support fabric lying along the side of said partition turned toward said upstream compartment;

means for passing through said chamber from said upstream compartment to said downstream compartment a carrier medium and entraining a particulate filter-aid layer onto said fabric in said upstream compartment;

means for passing a filterable medium through said chamber from said upstream compartment to said downstream compartment whereby said filterable medium traverses said layer and said fabric;

washing means including an inlet opening connectable with said chamber on the downstream side of the fabric and an outlet opening communicating with said upstream compartment at an upstream side of said fabric for passing a washing medium through said chamber from said inlet to said outlet opening and thereby backwashing said layer from said fabric and entraining material of said layer out of said chamber through said outlet opening; and a respective movable wall flanking each side of said partition and defining the respective compartment with said fabric, the side of said partition facing the wall of said downstream compartment being from a support fabric and said wall of said downstream compartment being sealingly engageable with said partition to block the throughgoing openings therein.

7. The filtering apparatus defined in claim 6 wherein said partition is formed with at least one grate and said wall of said downstream compartment includes rises aligned with said throughgoing openings and receivable therein to completely fill said throughgoing openings.

8. The filtering apparatus defined in claim 7 wherein said rises are formed on a displacement plate carried by said wall of said downstream compartment.

9. The filtering apparatus defined in claim 8 wherein said rises and said throughgoing openings converge toward said upstream compartment.

10. The filtering apparatus defined in claim 8 wherein said partition is formed by a fixed central bar and a bar of grates replaceably engaging said fixed central bar.

11. The filtering apparatus defined in claim 10 wherein said central bar is formed with at least some of said openings for the means for passing said carrier and filterable media through said compartment substantially at the center of said bar.

12. The filtering apparatus defined in claim 11 wherein said bar is provided with tubes communicating with said openings and each tube at a central region of each bar is sealingly connected therewith at the respective opening.

13. The filtering apparatus defined in claim 11 wherein said openings of the central region of said bar are juxtaposed with sealing surfaces of said movable walls and are closable thereby.

14. The filtering apparatus defined in claim 13 wherein each of the openings on said bar is juxtaposed with a displacement body carried by the respective movable wall.

* * * * *